(12) United States Patent
Pohl et al.

(10) Patent No.: US 7,141,394 B2
(45) Date of Patent: Nov. 28, 2006

(54) MORE STABLE ANALOG OF ISOPROPYL THIOGALACTOSIDE FOR INDUCTION OF PROTEIN EXPRESSION

(75) Inventors: Nicola Lucia Pohl, Ames, IA (US); Kwang-Seuk Ko, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 70 days.

(21) Appl. No.: 10/827,213

(22) Filed: Apr. 19, 2004

(65) Prior Publication Data

US 2004/0224390 A1  Nov. 11, 2004

Related U.S. Application Data

(60) Provisional application No. 60/463,871, filed on Apr. 18, 2003, provisional application No. 60/510,872, filed on Oct. 14, 2003.

(51) Int. Cl.
*C12P 21/04* (2006.01)
*C07H 7/02* (2006.01)

(52) U.S. Cl. .................. 435/70.1; 435/71.1; 536/1.11; 536/124

(58) Field of Classification Search ............... 536/1.11, 536/124; 435/70.1, 71.1
See application file for complete search history.

(56) References Cited

U.S. PATENT DOCUMENTS 6,174,867 B1 *  1/2001  Hindsgaul .................... 514/42

OTHER PUBLICATIONS

Baneyx, F. "Recombinant protein expression . . . " Curr. Opin. Biotechnol. (1999) vol. 10, pp. 411-421.*
Marquez, F. et al "Aplicacion de la reaccion de grignard . . . " Anales de Quimica (1983) vol. 79, pp 428-431.*
Wikipedia entry for "Lac Operon" http://en.wikipedia.org/wiki/Lac_operon—retrieved Dec. 22, 2005.*
USBiological product entry for "IPTG Dioxane Free" http://www.usbio.net/Product.aspx?ProdId=108—retrieved Dec. 22, 2005.*
Leveau, Johan H. J., et al.; "Predictive and Interpretive Simulation of Green Fluorescent Protein Expression In Reporter Bacteria" Journal of Bacteriology, Dec. 2001, p. 6752-6762.

* cited by examiner

*Primary Examiner*—Leigh C. Maier
(74) *Attorney, Agent, or Firm*—McKee, Voorhees & Sease, P.L.C.

(57) ABSTRACT

A novel C-glycoside of isopropylthiogalactoside (IPTG), isobutyl-C-galactoside (IBCG), is described. IBCG may be used as an IPTG substitute for increased induction of protein expression of plasmid-based genes for the production of recombinant proteins under the control of the lac promoter. IBCG offers the advantage over IPTG of being stable at ambient temperature.

19 Claims, No Drawings

US 7,141,394 B2

MORE STABLE ANALOG OF ISOPROPYL THIOGALACTOSIDE FOR INDUCTION OF PROTEIN EXPRESSION

CROSS-REFERENCE TO RELATED APPLICATIONS

This application claims priority to U.S. Provisional Application Ser. No. 60/463,871, filed Apr. 18, 2003, and hereby incorporated by reference in its entirety, and U.S. Provisional Application Ser. No. 60/510,872, filed Oct. 14, 2003, also hereby incorporated by reference in its entirety.

FIELD OF THE INVENTION

This invention relates to synthesis of a new chemical compound useful as an IPTG substitute for increased induction of protein expression.

BACKGROUND OF THE INVENTION

Addition of isopropyl-β-D-thiogalactopyranoside (IPTG) to bacterial cultures is a long-standing way to induce expression of plasmid-based genes for the production of recombinant proteins under the control of the lac promoter. IPTG binds to the lac repressor in *Escherichia coli*, thereby preventing binding of the repressor protein to DNA and blocking gene transcription.

There are several drawbacks to the use of IPTG. From the standpoint of experimental practicality, IPTG and its solutions should be stored well below room temperature (typically −20° C.) to prevent decomposition over time. In addition, multiple additions of IPTG are often necessary for longer induction times as the compound degrades under culture conditions.

There is therefore a need in the art for a more stable version of IPTG to circumvent the stability issues described above, and provide greater control of protein expression, especially over long periods of induction.

It is therefore a primary objective of the present invention to provide a new compound, method and means of inducing expression of genes for the production of recombinant proteins.

It is a further objective of the present invention to provide a new compound that may be used to induce expression of genes for the production of recombinant proteins, whereby the compound is stable at ambient temperatures.

It is still a further objective of the present invention to provide a new compound that may be used to induce expression of genes for the production of recombinant proteins that is easy to synthesize.

It is a further objective of the present invention to provide a new compound that may be used to induce expression of genes for the production of recombinant proteins that is a functional substitute of IPTG.

It is a further objective of the present invention to provide a new compound that may be used to induce expression of genes for the production of IPTG that is more convenient and economical to store and transport.

It is yet a further objective of the present invention to provide a new compound that may be used as a galactose substitute.

These and other objectives will become clear from the foregoing detailed description.

SUMMARY OF THE INVENTION

The present invention is directed to a novel compound that is a C-glycoside analog of IPTG, and which is preferably isobutyl-C-galactoside (IBCG). This compound may be used as a functional replacement of IPTG in inducing expression of proteins under control of the lac promoter, or for other IPTG applications. IBCG may also be used as a mimic or substitute for galactose.

The present invention is also directed to caged compounds of IBCG. Any acylated intermediate in the synthesis of IBCG is a caged compound.

IBCG offers several advantages over IPTG. First, unlike IPTG, IBCG is stable at room temperature, and therefore may be more conveniently and economically stored and transported. In addition, based on its improved stability, IBCG appears to be superior to IPTG in inducing protein expression during longer periods of induction.

DETAILED DESCRIPTION OF THE INVENTION

The present invention is predicated on the finding that the anomeric linkage of the natural inducer allolactose in IPTG does not form any critical binding interactions with the lac repressor protein. It appears that only the galactose portion of the larger carbohydrate is necessary to disrupt the repressor protein/DNA binding interaction. For instance, substitution of the 6-OH of galactose with methyl or hydrogen destroys its induction capabilities. Boos, W., et al. *Biochem.* 1967, 1, 328–394. In contrast, the sulfur of the galactosidic bond is not implicated in a particular binding interaction that would be destroyed in the absence of lone pairs, as seen by inspection of the recent X-ray structure of the *E. coli* lac repressor bound to IPTG. Lewis M., et al., *Science* 1996. 21, 1274–1254. The present inventors therefore hypothesized that substitution of the anomeric atom appeared feasible provided the increased conformational mobility of the carbon side chain did not interfere with binding or significantly diminish cell permeability.

Quite surprisingly, experimental results indicate that IBCG induces protein expression as well as IPTG, and even better at longer induction times. Further, unlike IPTG which must be stored at −20° C., IBCG is stable in solution at ambient temperature, and therefore does not require expensive freezer space for its storage and transport. This improved stability feature of IBCG also results in more accurate concentrations of the compound when used in experiments.

A schematic illustrating synthesis of IBCG and its subsequent induction of protein expression is set forth below:

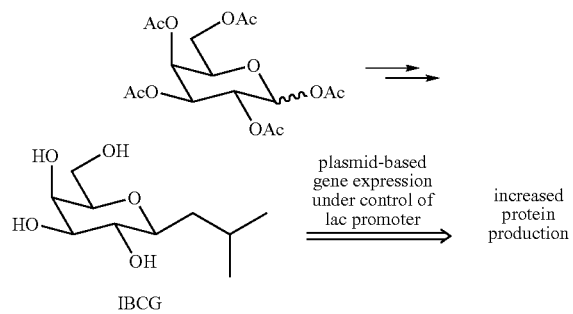

The invention describes a method and composition that may be used as a functional replacement of IPTG in inducing expression of proteins under control of the lac promoter. However, the present invention is expected to function in any lac-based system inducible by IPTG since IBCG is an analog of IPTG having similar properties thereto. Lac-based promoters such as lac, tac, trc are well known to those of skill in the art.

The IBCG may also be used as a galactose substitute, for such applications as lactose-free milk, whey products, in combination with other sugars as a laxative, measurement of liver function, ultrasound contrast, and for kits for determining galactosaemia. The invention embraces achiral, achiral diastereomers, racemic mixtures, as well as enantiomeric forms of IBCG.

The present invention is also directed to "caged" IBCG. Photosensitive precursors or "caging" groups are molecules which bind an "effector" molecule through a covalent bond to the photosensitive precursor group, thereby reversibly rendering the effector molecule inert (McCray et al., 1989). Caged compounds are artificial molecules whose biological activity is controlled by light, usually by photolytic conversion from an inactive to an active form. Photochemical cleavage of that single bond releases the active species. Caged compounds are most commonly designed by modifying a desired biomolecule with a suitable photoremovable protecting or "caging" group.

As used herein, the term "caged" is merely descriptive of the photo release property of these groups and does not refer to physical trapping of the inactivated substance within a crystal lattice. Caging groups have been used in a number of biological studies to study cell motility, muscle fibers, active transport proteins, biological membranes and other intracellular responses (e.g., Ishihara et al., 1997; Lee et al., 1997; Patton et al., 1991; see review by McCray et al., 1989). Caging groups have also been used in the caging of nucleotide analogues (Walker et al., 1988) and the synthesis of bio-chip arrays (McGall et al., 1996). Classically, caging groups have been used to study the time course of cellular responses induced by a step change in a local concentration of caged and subsequently, inactivated bio-chemical species, e.g., caged ATP.

A review of caged compounds and identification of many caging groups is described in "Controlling Cell Chemistry with Caged Compounds", Adams et al., *Annu. Rev. Physiol.*, 1993 55:755–84. Numerous other photolabile caging compounds have been reported in the literature, including benzyl bromides; 1-(.varies.-diazobenzyl)pyrene; N-hydroxy-2-thiopyridone; N-hydroxysuccinimidyl p-azidobenzoate; N-hydroxysuccinimidyl ester of p-azidobenzoylglycine; N-hydroxysuccinimidyl ester of p-benzoylbenzoate; p-pentachlorophenyl ester of p-benzoylbenzoylglycine; (bromomethyl)phenylacetate; 1-peptidyl-5-bromo-7-nitroindoline; as well as aromatic diazo compounds such as 1-(2-nitro-4,5-dimethoxy)phenyl-diazoethane, 1-(2-nitro)phenyl-diazoethane, and 1-(2-nitro-3,4,5,6-tetramethyl-diazoethane.

There are numerous ways of synthesizing IBCG, and the present invention is intended to encompass all such methods and means. Such methods may be readily determined by persons skilled in the art. Liu, L. et al., *Curr. Org. Chem.* (2001), 4, 1133–1167 (the disclosure of which is hereby expressly incorporated by reference) describe several possible procedures for synthesizing IPTG that may be modified to produce IBCG.

Two possible means of producing IBCG include (1) the galactose pentaacetate treatment method; and (2) Grignard reaction approach. In the first method, galactose pentaacetate is treated with methallyltrimethylsilane in the presence of boron trifluoride etherate, to give a mixture of α and β anomers, which are separated using silica gel column chromatography to provide the β-anomer. The drawback to this procedure is that while the scheme provides the desired compound following hydrogenation of the alkene and Zemplen deacylation, separation of the anomeric mixture is somewhat tedious.

A second approach to synthesizing IBCG relies on a Grignard reaction that has been previously applied to glucose derivatives. In this reaction, commercially available bromoacetogalactose, or other acetogalactose having a halide group, is treated with an excess of an organomagnesium halide (RMgX), such as isobutylmagnesium bromide, to provide exclusively the desired β-anomer of the C-linked glycoside. Deprotection of the acetyl groups with sodium methoxide results in the desired IBCG.

IBCG may be used in the same manner as IPTG for purposes of inducing protein expression, and for other IPTG applications as well. Therefore, these applications extend to the use of IPTG to regulate gene expression in plant cells. Plants can be produced which contain selected systems which allow for regulated expression of an introduced or endogenous gene. Inclusion of a gene of interest on a vector placing it under control of the lac operon permits expression of the gene in the presence of IPTG. Such regulatory systems are well known in the art. For instance, IPTG has been shown to relieve repression of tRNAs by the lac operator in plants as described by Ulmasov, B. et al. (1997), Regulated expression of plant tRNA genes by prokaryotic tet and lac repressor, *Plant Molecular Biology*, 35(4), 417–424, which is incorporated by reference. Further, the presence of IPTG in lacI protoplast has been demonstrated to provide relief of repression as described by Wilde, R. J. et al. (1992), Control of gene expression in tobacco cells using a bacterial operator-repressor system, *EMBO Journal*, 11(4), 1251–9, incorporated herein by reference. Therefore the present invention contemplates methods of regulating protein expression in plant cells.

For production of the polypeptides, host cells, such as a plant cell, can be genetically engineered to incorporate expression systems or portions thereof. Introduction of a constructs comprising the expression system into a plant cell can be effected by methods described in many standard laboratory manuals, such as Davis, et al., Basic Methods In Molecular Biology, (1986) and Sambrook, et al., Molecular Cloning: A Laboratory Manual, 2nd Ed., Cold Spring Harbor Laboratory Press, Cold Spring Harbor, N.Y. (1989). Practically, all plants are contemplated by the present invention including, but not limited to, to all major species of plants.

As already noted above, however, the primary difference is that IBCG does not require storage at −20° C. IBCG also has improved metabolic stability in comparison to IPTG.

A typical protein expression experiment consists of the following steps. First, a single colony from a freshly streaked plate of the expression host containing the recombinant vector is chosen. When the heterologous protein is toxic for the cells, higher expression levels are obtained by using the so-called "plating" method for culture inoculation. The protocol for this method is as follows: (1) A single colony of plasmid-containing cells is suspended in 200 ml water and vigorously shaken; (2) The suspension is plated on an LB plate containing the appropriate antibiotic and incubated overnight at 37° C.; (3) All colonies (typically 1000–10,000) are scraped off and suspended in 400 mL LB medium. This suspension usually has an $OD_{600}$ of approx. 0.4; (4) The culture can be grown to the desired OD and induced to start expression. Suter-Crazzolara, C. et al. (1995), Improved expression of toxic proteins in *E. Coli*. *BioTechniques* 19, 202–204.

The starter culture is then grown by inoculating with the chosen colony up to 50 mL of rich medium (such as LB or 2×YT) containing the appropriate antibiotic (kanamycin, ampicillin, etc.). When a larger starter culture is required, the rich media is preferably inoculated with 4 mL of the single colony, allowed to grow for 4–8 hours at 37° C., then this is used to inoculate the starter culture. Overnight cultures are preferably grown at 30° C. or lower. Alternatively, the culture can be incubated at 37° C. until the $OD_{600}$ is approximately 1, and the culture is stored at 4° C. overnight. The following morning, cells are collected by centrifugation, resuspended in fresh medium, and are then used to inoculate the main culture.

The main culture is then inoculated and incubated until the $OD_{600}$ reaches 0.4–1. The optimal OD value will depend on the culture method and medium. For flask cultures using LB-medium, an $OD_{600}$ of 0.6 is recommended. Protein expression is then induced by addition of IPTG (or IBCG) to a final concentration of about 0.05–2.0 mM. After induction, the cultures are incubated from 3 hours to overnight depending on the induction temperature (overnight for incubation temperature of 15–25° C., 5–6 hours for incubation temperature of 30° C., and 3–4 hours for incubation temperature of 37° C.). The cell pellet is then harvested by centrifugation (20 minutes at 6000 g).

The following example is offered to illustrate but not limit the invention. Thus, it is presented with the understanding that various formulation modifications as well as method of delivery modifications may be made and still are within the spirit of the invention.

EXAMPLE 1

Preferred IPTG/IBCG Induction Procedure for DE3 Lysogens

The following is a preferred IPTG induction procedure taken from Novagen, *pET System Manual*, 10th Edition, the disclosure of which is hereby expressly incorporated by reference. This method (including specific concentrations, procedures, etc.) is also preferred for induction using IBCG.

After a target plasmid is established in a λDE3 lysogen, expression of the target DNA is induced by the addition of IPTG to a growing culture. For pET constructions carrying the T7lac promoter, 1 mM IPTG is recommended for full induction. Detailed protocols for small scale induction, fractionation and analysis of expression of expression are given in Section VI, Target Protein Verification (page 52) of the *pET System Manual*.

Some λDE3 host strains allow variation of the expression level simply by varying the concentration of IPTG added to induce expression. The Rosetta™(DE3), Tuner™(DE3) and Origami™B(DE3) strains contain the lacY1 mutation eliminating the active transport of lactose into cells via lac permease. Therefore, these strains are less sensitive to lactose in the media and IPTG inductions results in a more uniform entry into all cells in the population. When using these strains, a range of IPTG concentrations from 25 μM to 1 mM should be tested, and the induced cultures examined for activity and solubility of the target protein to establish the optimal IPTG concentration for the desired result.

Preparation for Induction

Pick a single colony from a freshly streaked plate and inoculate 50 mL LB containing the appropriate antibiotic(s) for the plasmid and host strain in a 250 mL Erlenmeyer flask. For good aeration, add medium up to only 20% of the total flask volume.

Alternatively, inoculate a single colony or a few microliters from a glycerol stock into 2 mL LB medium containing the appropriate antibiotic for the plasmid and host strain. Incubate with shaking at 37° C. until the $OD_{600}$ reaches 0.6–1.0. Store the culture at 4° C. overnight. The following morning, collect the cells by centrifugation (30 sec in a microcentrifuge). Resuspend the cells in 2 mL fresh medium plus antibiotic and use this to inoculate 50 mL medium.

Sample Induction Protocol
1. Incubate with shaking at 37° C. until $OD_{600}$ reaches 0.4–1 (0.6 recommended; about 3h).
2. Add IPTG from a 100 mM stock to a final concentration of 1 mM and continue the incubation for 2–3 h.
3. Place the flasks on ice for 5 min and then harvest the cells by centrifugation at 5000 ×g for 5 min at 4° C. Save the supernatant, if desired, for further analysis.
4. Resuspend the cells in 0.25 culture volume of cold 20 mM Tris-HCl pH 8.0, and centrifuge as above.
5. Remove the supernatant and store the cells as a frozen pellet at −70° C. or continue with purification (note that inclusion bodies become less soluble upon aging in the freezer).

EXAMPLE 2

Synthesis of Isobutyl-C-agalactoside (IBCG) as an Isopropylthiogalactoside (IPTG) Substitute for Increased Induction of Protein Expression General methods: Reaction solvents were distilled from calcium hydride for dichloromethane and from sodium metal and benzophenone for diethyl ether. Amberlyst 15 ion-exchange resin was washed repeatedly with methanol before use. The Grignard reaction was performed in oven-dried glassware. The 1-bromo-α-D-galactose-tetraacetate was dissolved in anhydrous toluene and the solvent was removed under reduced pressure; the sample was then dried under high vacuum for 3 days. All other commercial reagents and solvents were used as received without further purification. The reactions were monitored and the $R_f$ values determined using analytical thin layer chromatography (tlc) with 0.25 mm EM Science silica gel plates (60F-254). The developed tlc plates were visualized by immersion in p-anisaldehyde solution followed by heating on a hot plate. Flash chromatography was performed with Selecto Scientific silica gel, 32–63 μm particle size. All moisture-sensitive reactions were performed in flame or oven-dried glassware under a nitrogen atmosphere. Bath temperatures were used to record the reaction temperature in all cases. All reactions were stirred magnetically at ambient temperature unless otherwise indicated. $^1H$ NMR and $^{13}C$ NMR spectra were obtained with a Bruker DRX400 at 400 MHz and 100 MHz respectively. $^1H$-$^1H$ correlation experiments were obtained with a Bruker Advance DRX500.

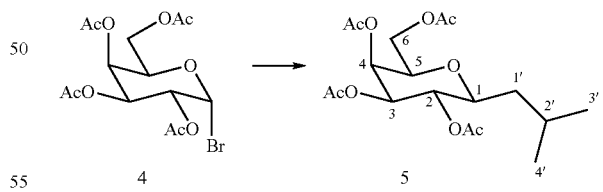

1-Isobutyl-β-D-galactose tetraacetate (5): Magnesium turnings (4.2 g) were suspended in diethyl ether (45 mL) and then initiated with a crystal of $I_2$. 1-Bromo-2-methylpropane (1.37 mL, 12 mmol) was then added to the magnesium suspension. The mixture turned a cloudy white after the flask was heated with α heat gun. A solution of 1-bromo-α-D-galactose tetraacetate 4 (4.307 g, 10.5 mmol) in diethyl ether (10 mL) was added dropwise into the Grignard reaction mixture. The reaction went to completion after the mixture was heated at reflux for 4 h. The mixture was slowly poured into water (300 mL). Glacial AcOH (11 mL) was added. The mixture was separated and the aqueous layer was concentrated. The residue was treated with acetic anhydride (150 ML) and pyridine (150 mL) overnight. The resulting mixture was diluted with water (300 mL), extracted with diethyl ether (3×250 mL), washed with water (2×150 mL), and dried with magnesium sulfate. The solvent was removed under reduced pressure. The product was purified by flash chromatography (silica gel, 2:3 ethyl acetate/hexane) to afford 5 as a white solid (2.80 g, 7.24 mmol, 69%).

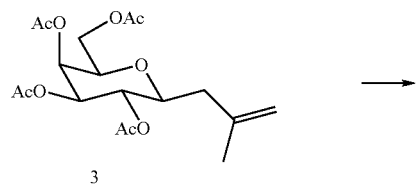

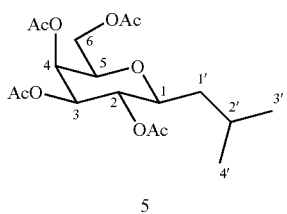

1-isobutyl-β-D-galactose tetraacetate (5): A solution of 3 (0.90 g, 2.3 mmol) in MeOH (15 mL) was stirred with 20 wt. % palladium hydroxide on carbon (0.08 g) under atmospheric $H_2$ at ambient temperature for 5 h. The mixture was filtered over Celite and the filtrate was concentrated under reduced pressure to afford 5 as a white solid (0.90 g, 2.3mmol, 97%).

$R_f$ 0.35 (ethyl acetate/hexane, 3/7 v/v). $^1$H NMR (400 MHz, $CDCl_3$)δ5.36(d,1 H, J=3.2 Hz H-4), 5.01 (dd, 1H, $J_1$=8.0 Hz, $J_2$=8.8 Hz, H-2),4.96 (dd, 1 H, $J_1$=3.2 Hz, $J_2$=8.0 Hz, H-3),4.10 (dd, 1 H, $J_1$=$J_2$=6.8 Hz, H-6), 3.99 (dd, 1 H, $J_1$=4.8 Hz, $J_2$=6.4 Hz, H-6), 3.79 (m, 1 H, H-5), 3.39 (dd, 1 H, $J_1$=9.0 Hz, $J_2$=2.0 Hz, H-1), 2.11 (s, 3 H, acyl), 2.00 (s, 3 H, acyl), 1.98 (s, 3 H, acyl), 1.94 (s, 3 H, acyl), 1.78 (m, 1 H, H-2'), 1.48 (m, 1 H, H-1'), 1.14 (m, 1 H, H-1'), 0.88 (d, 3 H, J=6.8 Hz, H-3' or H-4'), 0.83 (d, 3 H, J=6.4 Hz, H-3' or H-4'). $^{13}$C NMR (100 MHz, $CDCl_3$) δ 170.7, 170.6, 170.4, 170.1, 74.4, 72.5, 70.0, 68.0, 66.5, 61.9, 40.4, 24.5, 23.7, 21.7, 21.1, 20.9, 20.8. MS (EIMS) m/z 389 $[M+H]^+$

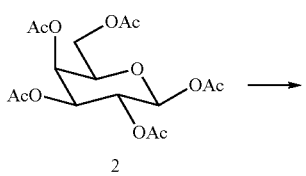

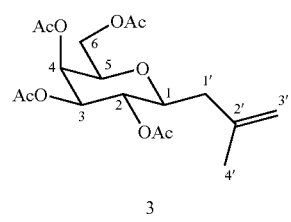

1-(2'-methylallyl)-β-D-galactose tetraacetate (3): To solution of β-D-galactose-pentaacetate (2.02 g, 5.18 mmol) in dichloromethane (60 mL) was added methallyltrimethylsilane (2.66 g, 20.7 mmol) followed by slow addition of $BF_3$-$Et_2O$ (1.64 mL) into the solution at −20° C. The mixture was stirred under $N_2$ overnight. The reaction was poured into a saturated solution of $NaHCO_3$. The product was extracted with dichloromethane (3×60 mL) and the solvent was removed under reduced pressure. The product was purified by flash chromatography (silica gel, ethyl acetate/hexane gradient) to yield a white solid (0.96 g, 2.5 mmol, 48%).

$R_f$ 0.23 (ethyl acetate/hexane, 3/7 v/v). $^1$H NMR (400 MHz, $CDCl_3$)δ5.38 (dd, 1 H, J=1.2 Hz, H-4), 5.08 (t, 1 H, $J_1$=9.9 Hz, $J_2$=6.9 Hz, H-2), 4.99 (dd, 1 H $J_1$=$J_2$=3.6 Hz, H-3), 4.73 (d, 2 H, J=17.1 Hz, H-3'), 4.11 (m, 1 H, H-6), 4.01 (dd, 1 H, $J_1$=$J_2$=6.6 Hz, H-6), 3.82 (t, 1 H, J=5.7 Hz, H-5), 3.54 (m, 1 H, H-1), 2.19 (m, 2 H, H-1'), 2.13 (s, 3 H, acyl), 2.03 (s, 3 H, acyl), 2.01 (s, 3 H, acyl), 1.96 (s, 3 H, acyl), 1.70 (s, 3 H, H-4'). $^{13}$C NMR (100 MHz, $CDCl_3$)δ170.6, 170.5, 170.4, 170.0, 141.6, 112.9, 77.3, 74.3, 72.4, 69.7, 68.0, 61.8, 40.4, 23.0, 21.2, 21.1, 20.9, 20.8.

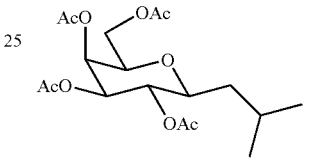

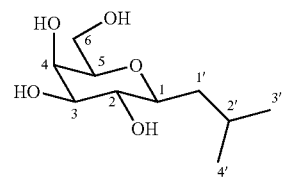

1-isobutyl-,β-D-galactose (1): 1-isobutyl-β-D-galactose tetraacetate 5 (1.21 g, 3.1 mmol) in MeOH (30 mL) was stirred with NaOH (0.22 g) at room temperature for 1.5 h. Amberlyst 15 ion-exchange resin was added to neutralize the solution. The mixture was filtered over Celite and methanol was evaporated under reduced pressure to afford 1 as a white solid (0.68 g, 3.1 mmol, 99%) [OR IS IT 0.086G, 0.89MMOL, 98%].

$R_f$ 0.28 (methanol/ethyl acetate/hexane, 1/5/5 v/v/v). $^1$H NMR (400 MHz, $D_2O$)δ3.76 (d, 1 H, J=4.4 Hz, H-4), 3.51 (m, 2 H, H-2, H-3), 3.41 (m, 1 H, H-5), 3.42 (m, 2 H, H-6), 3.25 (m, 1 H, H-1), 1.70 (m, 1 H, H-2'), 1.30 (m, 1 H, H-1'), 1.27 (m, 1 H, H-1'), 0.79 (d, 3 H, J=6.4 Hz, H-3' or H-4'), 0.75 (d, 3 H, J=6.4 Hz, H-3' or H-4'). $^{13}$C NMR (100 MHz, $D_2O$) δ 78.4, 78.2, 74.1, 71.5, 69.2, 61.3, 40.2, 23.9, 23.2, 20.9. MS (EIMS) m/z 221 $[M+H]^+$

EXAMPLE 3

To compare the ability of the C-glycoside to take the place of IPTG in the induction of protein expression, assays of promoter activity that rely on production of a fluorescent protein were pursued. Reporters for gene activity in bacteria that rely on green fluorescent protein (GFP) and its variants have become very popular as they have been validated by direct comparison to traditional reporter assays using either chloroamphenicol acetyltransferase or β-galactosidase. For bacterial studies, the enhanced green fluorescent protein (EGFP) is particularly useful as it is not toxic to *E. coli* like the wild type GFP itself and the protein folds and autocatalyzes formation of its fluorophore with a half-life of less than 45 minutes rather than hours. Therefore, the gene for EGFP (BD Biosciences) was ligated into a pET vector plasmid using NcoI and EcoRI in order to have control of EGFP protein expression with a lac promoter system and to have low background protein expression levels. This plasmid was transformed into *E. coli* BL21 DE(3) cells for protein expression studies. The cells were grown to an optical density of 0.7 (at 600 nm) and then protein production was induced with either IBCG or IPTG. The fluorescence emission at 507 nm after excitation at 488 nm, normalized for the number of cells, was plotted as a function of time (data not shown) as previously reported. As expected, in the absence of IBCG and IPTG, the culture showed no activity at the lac promoter. In contrast, EGFP fluorescence was considerably larger among induced cells in the presence of IBCG or IPTG. After induction times of greater than four hours, the IBCG induced cells show even greater fluorescence than the IPTG induced cells. This surprising result suggests that the C-glycoside analog may act as a superior promoter or that it is more stable in the culture conditions over time.

Clearly, the more stable C-glycoside analog IBCG serves as a surrogate for the commonly used inducer of protein expression IPTG and shows advantages at long induction times. In addition, solutions of the analog do not need to be made as frozen aliquots, but can be autoclaved in water and stored in room temperature for ready addition of the inducer to cell cultures. The latter property is especially valuable for small scale culture induction and for cases in which a more precise concentration of inducer is desirable. In addition, the C-glycoside retains cell permeability. This suggest that, in studies on biological systems dependent on O-glycosides, lone pairs in the glycosidic linkage are not necessarily required and the C-glycosides may offer distinct advantages beyond stability over S-glycosides in mimicking carbohydrate activities and functions.

It is understood that the present invention contemplates the use of not only the above-stated IBCG compound itself, but compounds which metabolize to IBCG and the analogues and biologically active salt forms thereof, as well as optical isomers which provide the same features and results.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All references contained herein are incorporated herein by reference in their entirety.

What is claimed is:

1. A compound that is effective in inducing expression of proteins under control of a lac-based promoter, said compound being stable at ambient temperatures, said compound being isobutyl-β-C-galactoside (IBCG), its biologically active salt forms, and optical isomers thereof.

2. The C-glycoside of claim 1 that is functionally equivalent to isopropyl-β-D-thiogalactopyranoside.

3. The compound of claim 1 that is stable at ambient temperatures.

4. The compound of claim 1 that is functional as a galactose substitute.

5. The compound of claim 1 wherein the lac-based promoter is selected from the group consisting of lac, tac, and trc.

6. The compound of claim 5 wherein the promoter is an *Escherichia coli* lac promoter.

7. A caged compound of formula:

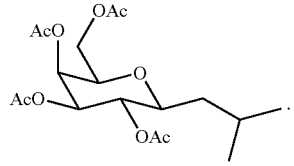

8. A method of inducing protein expression comprising: adding isobutyl-β-C-galactoside (IBCG), its biologically active salt forms, or optical isomers thereof to a bacterial culture.

9. The method of claim 8 whereby the bacterial culture is *Escherichia coli*.

10. The method of claim 9 whereby the IBCG binds with the lac repressor in the *Escherichia coli*.

11. The method of claim 8 whereby the IBCG is added to a final concentration of between about 0.05–2.0 mM.

12. The method of claim 8 that does not require multiple additions of the IBCG.

13. The method of claim 8 further including the step of storing the IBCG at ambient temperature.

14. A method of synthesizing isobutyl-β-C-galactoside (IBCG) comprising:
    treating galactose pentaacetate with methallyltrimethylsilane in the presence of boron trifluoride etherate.

15. A method of synthesizing isobutyl-β-C-galactoside (IBCG) comprising:
    treating a halo-acetogalactose with an excess of an organomagnesium halide to provide IBCG.

16. The method of claim 15 further including the step of deprotecting acetyl groups in C-linked glycoside with sodium methoxide.

17. A method of inducing protein expression comprising adding isobutyl-β-C-galactoside (IBCG) to a plant cell.

18. The method of claim 17 wherein the plant cell comprises an expression system having a lac-based promoter.

19. The method of claim 17 wherein the lac-based promoter is a lac promoter.

* * * * *